US011819593B2

(12) United States Patent
Verbeck, IV

(10) Patent No.: US 11,819,593 B2
(45) Date of Patent: Nov. 21, 2023

(54) REMOTE SMELL TECHNOLOGY

(71) Applicant: University of North Texas, Denton, TX (US)

(72) Inventor: Guido Fridolin Verbeck, IV, Lewisville, TX (US)

(73) Assignee: University of North Texas, Denton, TX (US)

(*) Notice: Subject to any disclaimer, the term of this patent is extended or adjusted under 35 U.S.C. 154(b) by 666 days.

(21) Appl. No.: 16/643,637

(22) PCT Filed: Aug. 31, 2018

(86) PCT No.: PCT/US2018/049199
§ 371 (c)(1),
(2) Date: Mar. 2, 2020

(87) PCT Pub. No.: WO2019/050803
PCT Pub. Date: Mar. 14, 2019

(65) Prior Publication Data
US 2021/0000998 A1    Jan. 7, 2021

Related U.S. Application Data

(60) Provisional application No. 62/555,393, filed on Sep. 7, 2017.

(51) Int. Cl.
*A61L 2/12* (2006.01)
*A61L 9/12* (2006.01)
*G16C 20/90* (2019.01)

(52) U.S. Cl.
CPC ............ *A61L 9/125* (2013.01); *G16C 20/90* (2019.02); *A61L 2209/11* (2013.01); *A61L 2209/131* (2013.01); *A61L 2209/133* (2013.01)

(58) Field of Classification Search
CPC .......................... A61L 9/125; A61L 2209/131
See application file for complete search history.

(56) References Cited

U.S. PATENT DOCUMENTS 5,832,320 A    11/1998    Wittek
6,548,025 B1    4/2003    Rasouli et al.
(Continued)

FOREIGN PATENT DOCUMENTS

WO    WO-2017134166 A1 *    8/2017    ............. A61G 11/00

OTHER PUBLICATIONS

International Search Report and Written Opinion issued for PCT Application No. PCT/US2018/049199, dated Jan. 2, 2019, 14 pages.

*Primary Examiner* — Elizabeth A Robinson
*Assistant Examiner* — Changru Chen
(74) *Attorney, Agent, or Firm* — Norton Rose Fulbright US LLP

(57) ABSTRACT

The present application relates to systems, methods, and computer-readable media for providing generating odors. In aspects, the disclosed methods may include generating, by a chemistry dispersion element, a signal configured to act upon a surface of a chemistry reservoir to disperse an odorous substance retained within the chemistry reservoir. The chemistry reservoir and the chemistry dispersion element may be disposed within a housing. The method also includes generating, by an air pump, a volume of air, and transporting, by an airflow pathway, the volume of air from the air pump to an air outlet. The volume of air passes through at least a portion of the housing as it flows through the airflow pathway from the air pump to the air outlet, and transports at least a portion of the odorous substance dispersed by the chemistry reservoir within the housing to the air outlet.

11 Claims, 14 Drawing Sheets

(56) References Cited

U.S. PATENT DOCUMENTS

| | | |
|---|---|---|
| 7,135,033 B2 | 11/2006 | Altshuler et al. |
| 2010/0155414 A1 | 6/2010 | Hu |
| 2016/0174812 A1* | 6/2016 | Artsyukhovich .... G02B 3/0012 |
| | | 65/387 |

* cited by examiner

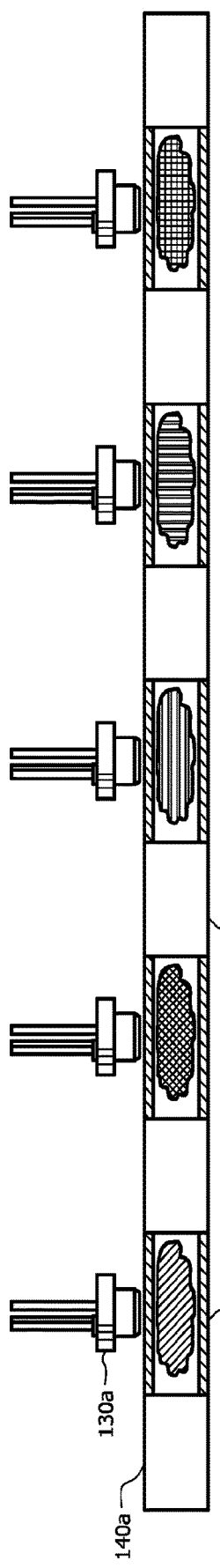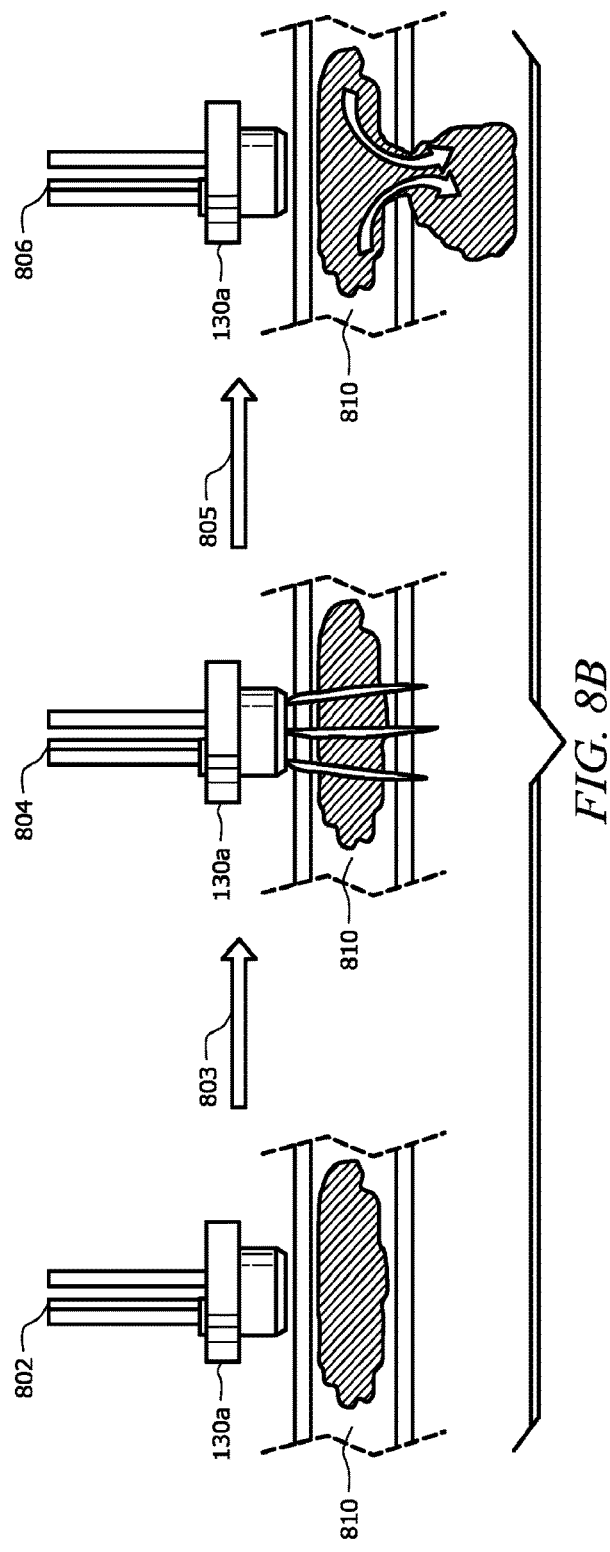

REMOTE SMELL TECHNOLOGY

CROSS-REFERENCE TO RELATED APPLICATION

This application is a national phase application under 35 U.S.C. § 371 of International Application No. PCT/US2018/049199 filed Aug. 31, 2018, which claims priority to U.S. Provisional Patent Application No. 62/555,393 filed Sep. 7, 2017. The entire contents of each of the above-referenced disclosures is specifically incorporated by reference herein without disclaimer.

TECHNICAL FIELD

The present application relates to remote smell technology, and more particularly to an improved architecture for implementing remote smell technology.

BACKGROUND

Remote smell technology offers many opportunities to enhance experiences across a variety of industries. For example, in the entertainment industry remote smell technology is viewed as a way to enhance movies, plays, video games, and the like by producing smells designed to mimic what the viewer sees. While remote smell technology has been the subject of much research and development, large scale deployments of remote smell technology have failed to gain widespread acceptance due to high deployment costs. Another hindrance to widespread adoption and deployment of remote smell technology stems from difficulties that arise once a scent has been dispersed. For example, if a dispersed scent lingers too long it may interfere with another scent that is subsequently dispersed. This reduces and/or eliminates the intended effects of the subsequently dispersed scent, and may detract from the viewer's overall experience.

SUMMARY

The present application is directed to systems, method, and computer-readable media configured to dispense odorous substances configured to simulate one or more smells. In aspects, one or more chemistry reservoirs may be provided and may retain odorous substances that, when dispersed, cause one or more smells to be perceived by a user. In aspects, chemistry dispersion elements are provided and configured to act upon the chemistry reservoirs to initiate dispersal of the odorous substances to create one or more desired smells. In aspects, the particular arrangement of the chemistry reservoirs and/or the chemistry dispersion elements may enable a device for generating smells that has a reduced foot print or form factor to be realized. Additionally, devices for generating smells in accordance with aspects of the present disclosure may operate with a reduced power consumption, making the devices more suitable for mobile deployments. Further, devices for generating smells in accordance with aspects of the present disclosure may be dynamically reconfigured to produce different smells and are modular, enabling the devices to be repaired more easily and at lower cost.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawings, in which:

FIG. 1 illustrates a block diagram of a system for mixing and dispensing odorous substances configured to simulate one or more smells in accordance with an embodiment of the present application;

FIG. 2 illustrates aspects of a chemistry dispersion element configured in accordance with an embodiment of the present application;

FIG. 3 illustrates aspects of a chemistry reservoir in accordance with an embodiment of the present application;

FIGS. 8A and 8B illustrate aspects of a technique for controlling a chemistry dispersion element to act upon a chemistry reservoir to disperse an odorous substance retained within the chemistry reservoir in accordance with an embodiment of the present application;

DETAILED DESCRIPTION

Figure 4A:
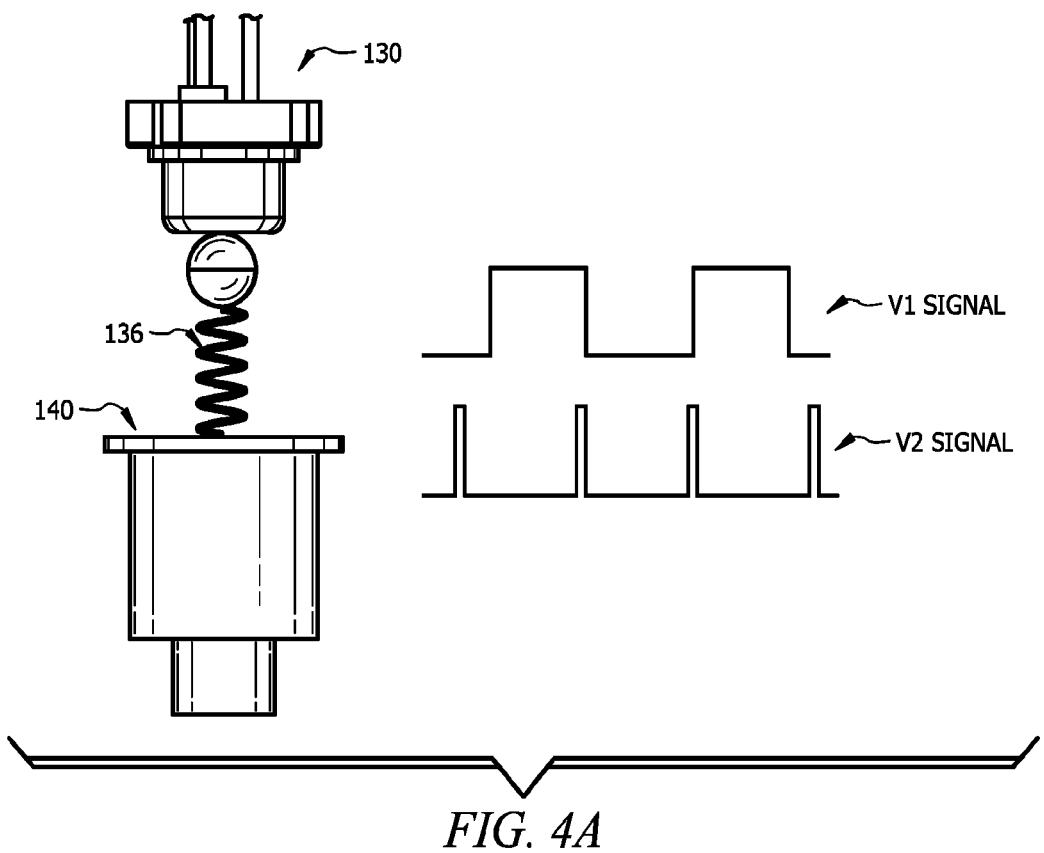
FIG. 4A illustrates aspects of a technique for controlling a chemistry dispersion element to act upon a chemistry reservoir to disperse an odorous substance retained within the chemistry reservoir in accordance with an embodiment of the present application.

Various features and advantageous details are explained more fully with reference to the non-limiting embodiments that are illustrated in the accompanying drawings and detailed in the following description. Descriptions of well-known starting materials, processing techniques, components, and equipment are omitted so as not to unnecessarily obscure the invention in detail. It should be understood, however, that the detailed description and the specific examples, while indicating embodiments of the invention, are given by way of illustration only, and not by way of limitation. Various substitutions, modifications, additions, and/or rearrangements within the spirit and/or scope of the underlying inventive concept will become apparent to those skilled in the art from this disclosure.

Figures 1, 2, 3:
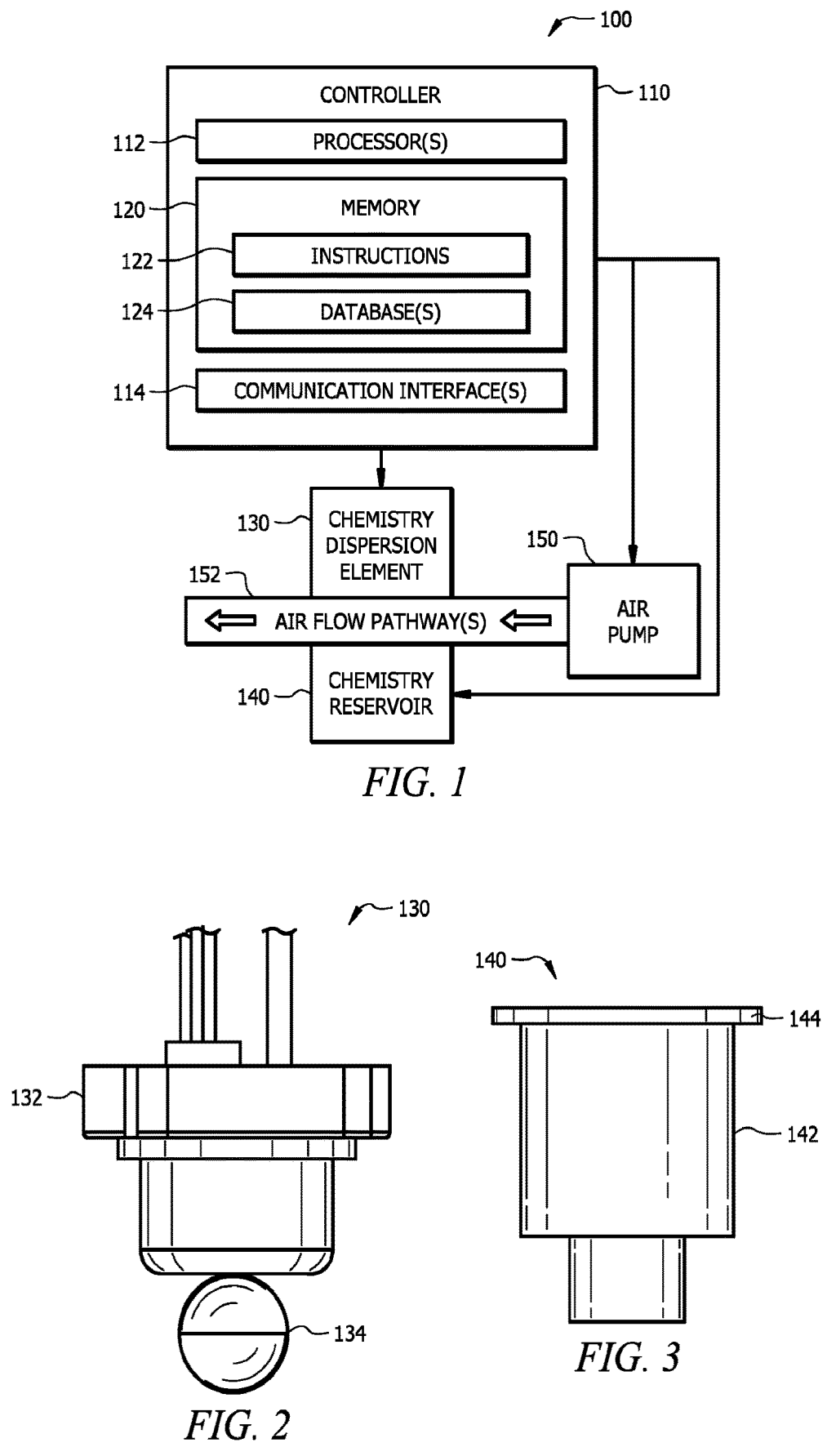

Referring to FIG. 1, a block diagram of a system for mixing and dispensing odorous substances configured to simulate one or more smells in accordance with an embodiment of the present application is shown as a system 100. As shown in FIG. 1, the system includes a controller 110, a plurality of chemistry dispersion elements 130, a plurality of chemistry reservoirs 140, an air pump 150, and one or more airflow pathways 152. As described in more detail below, the system 100 may be configured to dynamically mix and/or dispense one or more odorous substances to simulate one or more smells.

The plurality of chemistry reservoirs 140 may each be configured to retain odorous substances, and the plurality of chemistry dispersion elements 130 may be configured to act upon surfaces of particular ones of the plurality of chemistry reservoirs 140 to disperse one or more odorous substances from within the one or more chemistry reservoirs 140. Referring briefly to FIG. 2, aspects of an embodiment of a chemistry dispersion element 130 configured in accordance with an embodiment of the present application are shown. As shown in FIG. 2, in an embodiment, each of the plurality of chemistry dispersion elements 130 may include a laser diode 132 and a sapphire ball 134. The laser diode 132 may be configured to generate a laser signal that acts upon a surface of one of the plurality of chemistry reservoirs 140 to disperse the odorous substance retained therein. The sapphire ball 134 may be configured to focus the laser signal onto the surface of the chemistry reservoir 140.

Referring to FIG. 3, aspects of an embodiment of a chemistry reservoir in accordance with an embodiment of the present application are shown. As shown in FIG. 3, each of the plurality of chemistry reservoirs 140 may include a well 142 configured to retain an odorous substance, and a permeable membrane 144 covering at least a portion of the well 142. In aspects, the permeable membrane 144 may be configured to be biased to prohibit dispersion of the odorous substance retained within the well 142, but to enable the odorous substance retained within well 142 to pass through the permeable membrane 144 in response to being acted upon by one of the chemistry dispersion elements 130. In aspects, the permeable membranes 144 may be formed from polytetrafluoroethylene (PTFE), fluorinated ethylene propylene (FEP), polyether ether ketone (PEEK), ethylene chlorotrifluoroethylene (ECTFE), EFEP, which is a terpolymer (e.g., meaning it is composed of three parts) made from ethylene, tetrafluoroethylene (TFE), and hexafluoropropylene (HFP), ethylene tetrafluoroethylene (ETFE), liquid crystal polymers (LCPs), nylon, polyethylene (PE), polyethylene terephthalate (PET), perfluoroalkoxy (PFA), polyvinylidene fluoride (PVDF), THV, which is a polymer comprised of three different monomers: tetrafluoroethylene, hexafluoropropylene, and vinylidene fluoride, polydimethylsiloxane, nafion, or other materials that enable controlled dispersion of odorous substances retained therein.

The odorous substances retained within one or more of the plurality of chemistry reservoirs may include at least one of alkenes, alkanes, alcohols, phenols, aldehydes, esters, acids, aliphatics, aromatics, ketones, and steroids. In aspects, each of the plurality of chemistry reservoirs may retain only a single odorous substance. In additional aspects, one or more of the plurality of chemistry reservoirs may retain two or more odorous substances. Table 1 below illustrates exemplary odorous substances that may be retained within the plurality of chemistry reservoirs in accordance with aspects of the present disclosure.

TABLE 1

| | |
|---|---|
| Alkenes | α-pinene, caryophylene, D-limonene, dentadecene |
| Alkanes | eicosane, hexadecane, pentadecane, tetradecane, tridecane, dodecane, 4-phenyltridecane, 3-methyloctadecane, 3-methylnonadecane |
| alcohols and phenols | cedrol, 2-ethyl hexanol, 5-methyl-2-isopropyl cyclohexanol, benzyl alcohol, hexadecanol, phenol, 2-phenylethanol, 1-tridecanol, tetrade canol, geraniol, 2-hexanol, 3-hexanol, butanol, eugenol |
| aldehydes | benzaldehyde, decanal, nonanal, 2-nonenal, hexanal, heptanal, octanal, undecanal, dodecanal, geranial, tridecanal, and lilial |
| Esters | methyl salicylate, isobornyl propionate, hexadecanoic acid methyl ester, hexadecanoic acid dimethyl ester, nonanoic acid methyl ester, tridecanoic acid methyl ester |
| Acids | 7-octenoic acid, propanoic acid, butanoic acid, hexanoic acid, heptanoic acid, octanoic acid, nonanoic acid, decanoic acid, undecanoic acid, dodecanoic acid, 3-methyl-2-hexenoic acid, 2-methylhexanoic, 2-methylheptanoic, 2-methyloctanoic, 2-ethylhexanoic, 4-ethyldecanoic, acetic acid, lactic acid |
| aliphatics/aromatics | naphthalene, nonane, toluene |
| Ketones | 6-methyl-5-hepten-2-one, 2-propanone (or acetone) |
| Steroids | cholesterol, squalene, 5a-androst-16-en-3a-ol, 5a-androst-16-en-3b-ol, 5a-androst-16-en-3-one |
| Miscellaneous | diphenyl ether, tetramethyl thiourea, acetophenone |

It is noted that the exemplary odorous substances listed in Table 1 have been provided for purposes of illustration, rather than by way of limitation, and that the odorous substances retained within the chemistry reservoirs 140 of system 100 may include other odorous substances in accordance with aspects of the present disclosure.

Referring briefly to FIG. 4A, aspects of an embodiment for controlling a chemistry dispersion element to act upon a chemistry reservoir to disperse an odorous substance in accordance with an embodiment of the present application are shown. As shown in FIG. 4A, a chemistry dispersion element 130 may generate a laser signal 136 that acts upon a surface of a permeable membrane 144 of a corresponding one of the plurality of chemistry reservoirs 140 to disperse the odorous substance retained in the well 142. In aspects, the laser signal may be modulated to control the amount of the odorous substance that is dispersed in response to the chemistry dispersion element 130 acting upon (e.g., emitting the laser signal 136) the permeable membrane 144. For example, in FIG. 4A, a first signal V1 and a second signal V2 are illustrated. The different signals may be configured to control an amount of the odorous substance that is dispersed as a result of the chemistry dispersion element acting upon the permeable membrane of the chemistry reservoir. For example, the first signal V1 may disperse a first volume of the odorous substance and the second signal V2 may disperse a second volume of the odorous substance, where the first volume is greater than the second volume. In aspects, the first signal V1 may be generated by modulating the chemistry dispersion element 130 according to first modulation scheme, and the second signal V2 may be generated by modulating chemistry dispersion element 130 according to second modulation scheme. In aspects, the modulation of the chemistry dispersion element 130 may include pulse width modulation. It is noted that using pulse width modulation to control characteristics of the signal emitted by the chemistry dispersion element 130 has been provided for purposes of illustration, rather than by way of limitation, and that in other aspects of the present disclosure, other techniques may be used to control, adjust, and/or modify characteristics of the laser signal emitted by the chemistry dispersion element 130.

Figure 4B:
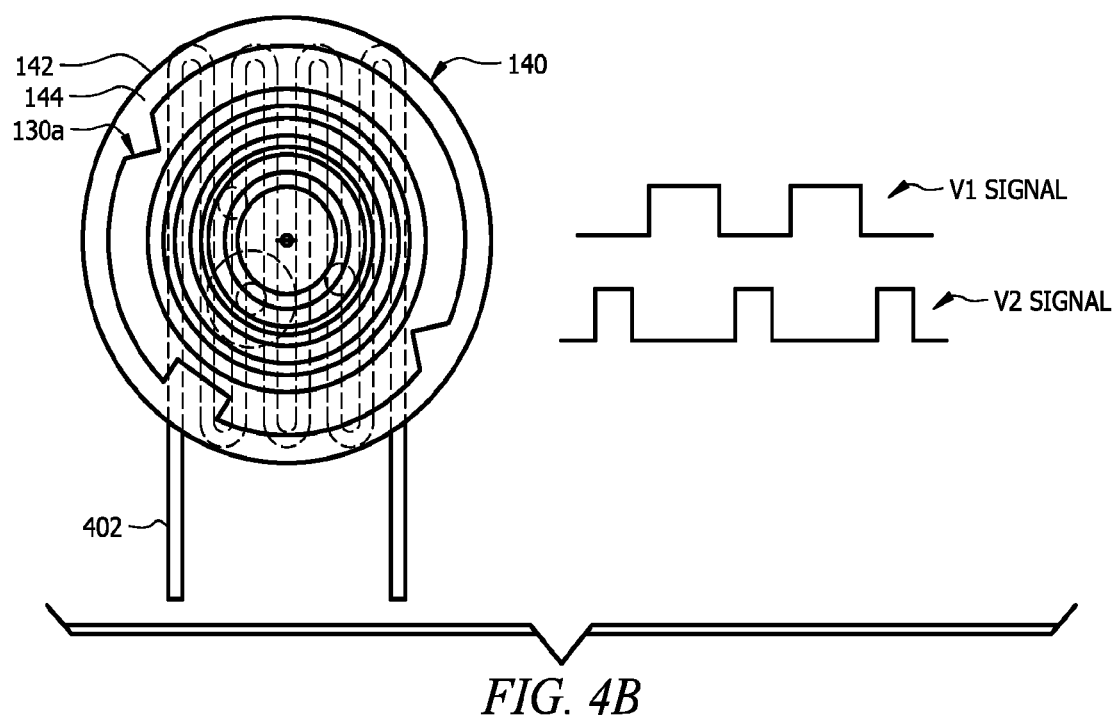
FIG. 4B illustrates additional aspects of a technique for controlling a chemistry dispersion element to act upon a chemistry reservoir to disperse an odorous substance retained within the chemistry reservoir in accordance with an embodiment of the present application.

Referring briefly to FIG. 4B, additional aspects of an embodiment for controlling a chemistry dispersion element to act upon a chemistry reservoir to disperse an odorous substance in accordance with an embodiment of the present application are shown. As shown in FIG. 4B, a chemistry dispersion element 130a may include a filament 402 configured to act upon a surface of a permeable membrane 144 of a corresponding one of the plurality of chemistry reservoirs 140 to disperse the odorous substance retained in the well 142. In aspects, the filament 402 may be formed from Nichrome wire and/or Tungsten wire, which may enable the filament 402 to be heated quickly, thereby providing a fast filament. In additional aspects, the filament 402 may be formed from another metal, alloy, or other material. In aspects, the filament 402 may be pulsed with a current to control the amount of the odorous substance that is dispersed in response to the chemistry dispersion element 130a acting upon (e.g., applying heat to) the permeable membrane 144. For example, in FIG. 4B, a first signal V1 and a second signal V2 are illustrated. The different signals may be configured to control an amount of the odorous substance that is dispersed as a result of the chemistry dispersion element acting upon the permeable membrane of the chemistry reservoir. For example, the first signal V1 may disperse a first volume of the odorous substance and the second signal V2 may disperse a second volume of the odorous substance, where the first volume is greater than the second volume. In aspects, the first signal V1 may be generated by pulsing the filament 402 of the chemistry dispersion element 130a with a first current pulsing scheme, and the second signal V2 may be generated by pulsing filament 402 chemistry dispersion element 130a according to second current pulsing scheme. In aspects, the pulsing scheme applied to the filament 402 of the chemistry dispersion element 130a may include pulse width modulation. It is noted that using pulse width modulation to control characteristics of the current applied to the filament 402 has been provided for purposes of illustration, rather than by way of limitation, and that in other aspects of the present disclosure, other techniques may be used to control, adjust, and/or modify characteristics of the laser signal emitted by the chemistry dispersion element 130.

Referring back to FIG. 1, the controller 110 may include one or more processors 112, one or more communication interfaces 114, and a memory 120. The one or more communication interfaces 114 may include input/output (I/O) communication interfaces, such as interfaces to one or more peripheral devices (e.g., a mouse, a keyboard, and the like), a network communication interface configured to communicatively couple the controller 110 (and the system 100) to one or more networks, and interfaces that communicatively couple the controller 110 to the plurality of chemistry dispersion elements 130, the plurality of chemistry reservoirs 140, and the air pump 150. In aspects, the memory 120 may store instructions 122 that, when executed by the one or more processors 112, cause the one or more processors 112 to perform operations for selectively generating and dispersing one or more smells in accordance with embodiments of the present disclosure, as described in more detail below. In aspects, the memory 120 may store a database 124. In aspects, the database 124 may store control information for controlling the selective generation and dispersion of the one or more smells, as described in more detail below.

The air pump 150 may be configured to generate a volume of air and the airflow pathways 152 may be configured to transport the volume of air from the air pump to an air outlet (not shown in FIG. 1). In an aspect, as the volume of air is generated by the air pump, an air flow current may be generated, which causes the volume of air to be transported through the air flow pathways 152. As the volume of air is transported through the air flow pathways, it may pass by the plurality of chemistry dispersion elements 130 and the plurality of chemistry reservoirs 140. As the volume of air flows through the air flow pathways 152 and past the plurality of chemistry dispersion elements 130 and the plurality of chemistry reservoirs 140, at least a portion of any odorous substances dispersed from the plurality of chemistry reservoirs 140 may be caught in the air flow and may travel to the air outlet, which may be located proximate a location configured to direct a smell corresponding the dispersed odorous substances towards a person, thereby causing the person to perceive the smell.

Figure 5A:
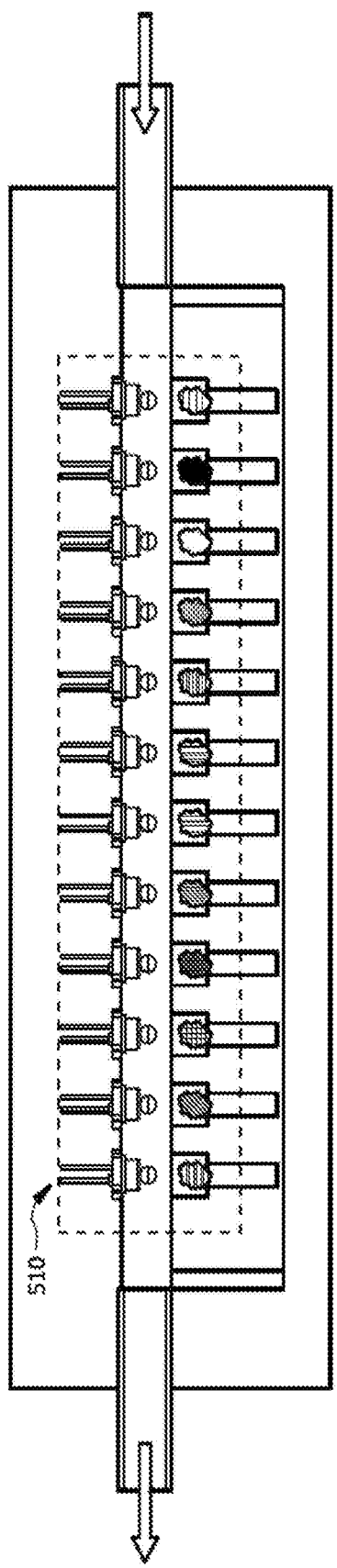
FIGS. 5A-5C illustrate aspects of a technique for dispensing one or more odorous substances in accordance with an embodiment of the present application.
Figure 5B:
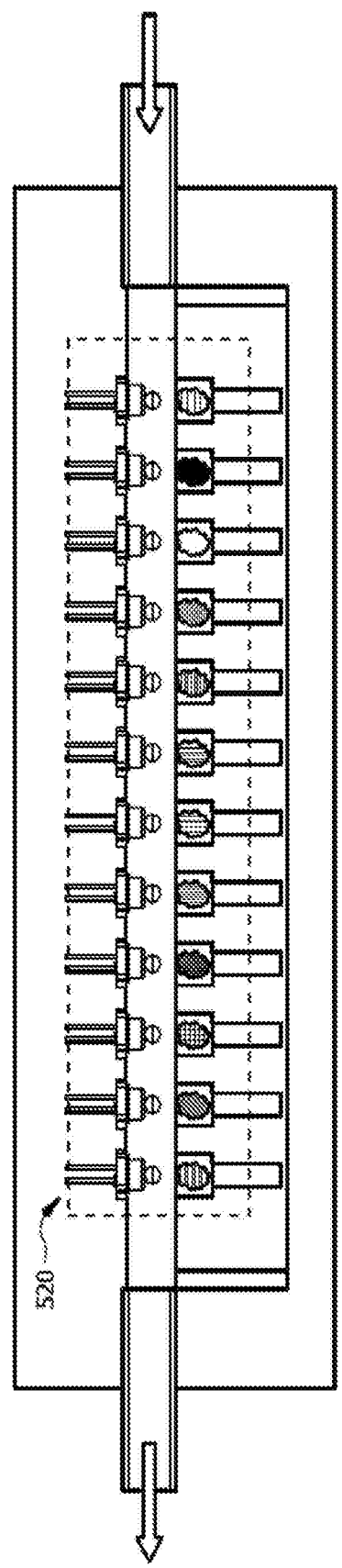
Figure 5C:
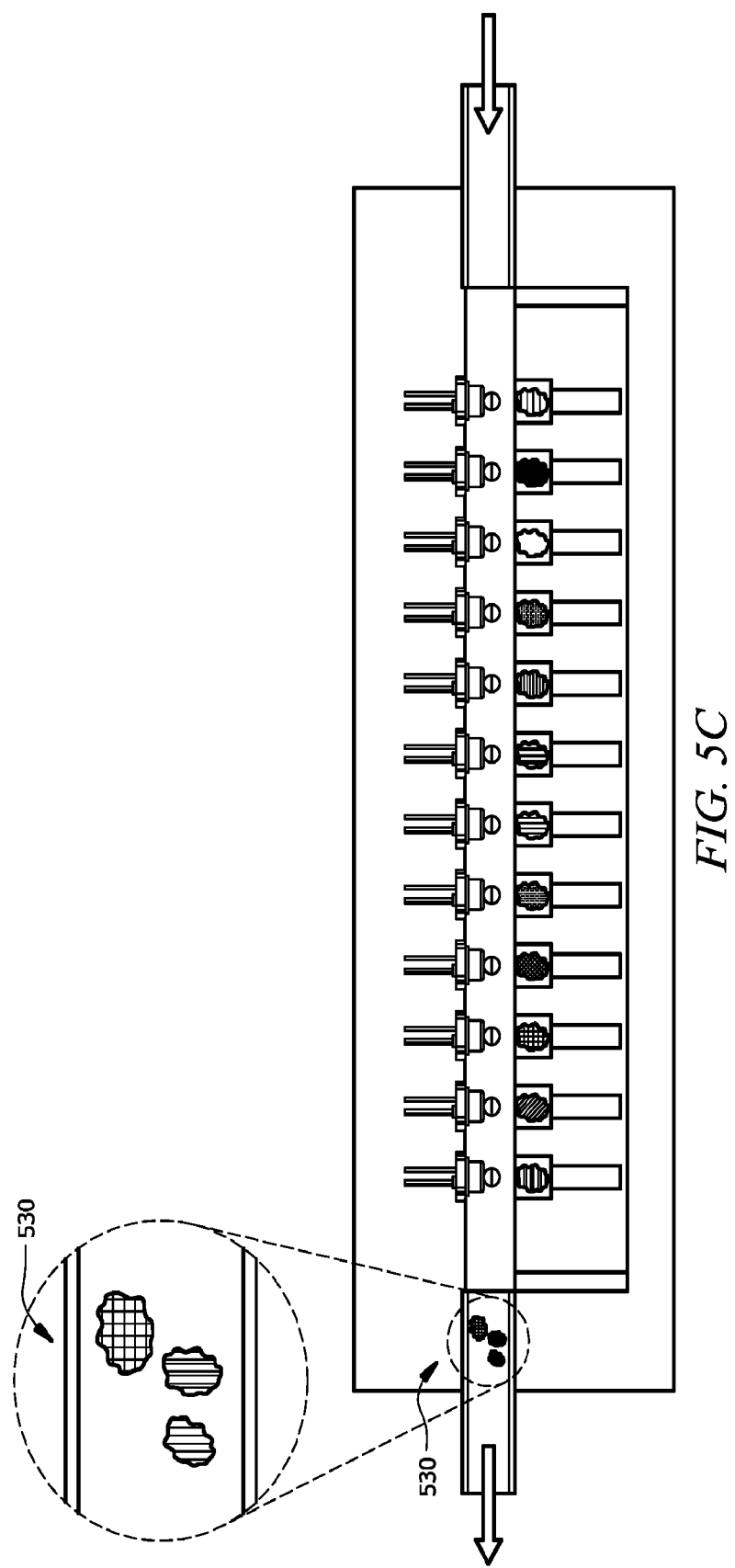

For example, and referring to FIGS. 5A-5C, aspects of a technique for dispensing one or more odorous substances in accordance with an embodiment of the present application are shown. In FIG. 5A, the plurality of chemistry dispersion elements 130 and the plurality of chemistry reservoirs 140 are shown. Additionally, an air flow is shown by the arrows, where the inlet is indicated by the arrow on the right side of FIG. 5A and an outlet flow of air is indicated by the arrow on the left side of FIG. 5A. As shown in callout 510, the plurality of chemical reservoirs each contain an odorous substance which is retained entirely within the respective wells of each of the chemical reservoirs. As shown in callout 520 of FIG. 5B, three of the plurality of chemistry dispersion elements (e.g., the third, sixth, and eighth chemistry dispersion elements starting from the left-hand side) have been activated (e.g., by controller 110 of FIG. 1), causing a portion of the odorous substances to be dispersed from the corresponding chemistry reservoirs. In callout 530 of FIG. 5C, it is shown that as the odorous substances are dispersed, at least a portion of the dispersed odorous substances are mixed in with the air flow, causing the dispersed odorous substances to be transported towards the air outlet, where they are transported by the air flow pathways (e.g., the air flow pathways 152 of FIG. 1) to the air outlet where one or more smells corresponding to the dispersed odorous substances may be perceived by one or more persons.

Referring back to FIG. 1, in aspects, the system 100 may be utilized to enhance various types of experiences for individuals. For example, the system 100 may be configured to enhance a virtual reality (VR) experience by generating smells corresponding to images and/or scenes depicted to a user via a virtual reality system, which may increase the immersive effect of the virtual reality experience for the user. In this example, the particular smells may be determined based on one or more scenes associated with media content, such as scenes from a movie, a video game, a play, and the like, and generation of the smells may be synchronized to presentation of those one or more scenes.

In aspects, the database 124 may store information that specifies a sequence of smells, and the controller may selectively activate particular chemistry dispersion elements of the plurality of chemistry dispersion elements 130 based on the sequence of smells. In this aspect, the sequence of smells may include information that identifies an activation sequence for activating, by the controller 110, particular ones of the plurality of chemistry dispersion elements 130, and timing information that indicates when the controller 110 is to activate each chemistry dispersion element 130 identified in the activation sequence. In this manner, the system 100 may be used to generate a plurality of different smells corresponding to particular portions of media content presented to a user. In aspects, the sequence of smells may include information that identifies the sequence of smells and timing information that indicates when the controller is to generate each smell identified in the sequence of smells. The database 124 may include information that maps smells to particular odorous substances retained within each of the plurality of chemistry reservoirs, and the controller may be configured to determine which ones of the particular chemistry dispersion elements are to be activated to generate the sequence of smells in accordance with the timing information. In aspects, the controller 110 may further be configured to determine a flow rate for the volume air and/or signal types for various instances where smells are generated. For example, higher flow rates and/or shorter pulses (e.g., by the chemistry dispersion elements) may be used to generate smells that are perceived by the user only briefly, while lower flow rate and/or longer pulses may be used to generate smells that are perceived more intensely by, or for a longer duration by, the user.

In aspects, timing information may synchronize the generation of the smells with particular aspects of visual content being presented to a user. For example, if the user were watching a move or television show including a scene where an actor walks into a home and smells freshly baked cookies, the sequence of smells may indicate particular chemistry dispersion elements that are to be activated to disperse odorous substances from one or more chemistry reservoirs in manner that is designed to mimic the smell of freshly baked cookies, and the activation of these a particular chemistry dispersion elements and chemistry reservoirs may by synchronized by timing information such that the smell of freshly baked cookies is perceived by the user at substantially the same time as the actor is portrayed as perceiving this smell. This may create an immersive effect that improves the viewing experience for the user.

In aspects of embodiments, the plurality of chemistry dispersion elements 130 and the plurality of chemistry reservoirs 140 may be arranged in a form factor that has a small footprint, enabling the system 100 to be deployed as a portable system for mixing and dispensing odorous substances configured to simulate one or more smells in accordance with an embodiment of the present application. In aspects, by configuring the plurality of chemistry dispersion elements as the laser diodes 132, as described above with reference to FIG. 2, the system 100 may consume less power than if filaments were used. For example, the laser diodes may consume 5 mw of power. If filaments were used instead of the laser diodes, they would consume 20-30 mw of power. Thus, by configuring the chemistry dispersion elements 130 as laser diodes, power consumption of the system 100 may be significantly reduced. This may enable the system 100 to be provided in a portable form factor, which may be particularly suited for certain types of deployments, such as deployments suitable for theme park rides where a person wears a pair of 3D glasses or other device as part of the experience and/or home applications, such as deployments of the system 100 for use during a video game session. In aspects, the system 100 may further include a power source (not shown in FIG. 1) that is configured to provide operational power to the plurality of chemistry dispersion elements 130. For example, in aspects, the power source may be a battery. In additional or alternative aspects, the power source may be a power generation system of a building (e.g., a power source that draws power from a power grid and/or a generator), such as through a plug being inserted into an outlet. In an additional or alternative aspect, the power source may be provided by an external device interface, such as a universal serial bus (USB) port on a gaming console or other external device or peripheral device.

Additionally, it is noted that the system 100 may be configured to disperse finely tuned quantities of odorous substances, enabling the system 100 to disperse smells at different intensity levels. For example, by varying the laser signal output by the chemistry dispersion elements 130, as described above with reference to FIG. 2, the odorous substances may be dispersed in concentrations ranging from "X" parts per million to "X" parts per trillion, enabling the system 100 to disperse odorous substances configured to exhibit smells across a variety of different intensity levels. Thus, when a smell corresponding to a visual scene is intended to be subtle (e.g., as if the smell were originating from a distance), the system 100 may disperse a smaller quantity of one or more odorous substances retained within one or more of the chemistry reservoirs 140, and when the smell is intended to be more intense (e.g., the smell is coming from close by), the system 100 may disperse a larger quantity of the one or more odorous substances. It is noted that other factors may also contribute to the ability of the system 100 to vary the intensity of the smells created by dispersing the odorous substances retained within the plurality of chemistry reservoirs 140. For example, a thickness and/or porosity of the permeable membrane 144 covering particular ones of the wells 142 may be varied, where thicker permeable membranes 144 and/or smaller pore size may decrease the intensity of the smells (e.g., increase the subtlety of the smells), and thinner permeable membranes 144 and/or larger pore sizes may increase the intensity of the smells (e.g., make the smells appear to be originating from nearby).

Further, by reducing the form factor and power consumption of a system configured to disperse chemical substances, systems for delivering more than just smells synchronized to media content may be realized. For example, in aspects, system 100 may be configured to dispense micro-doses of various drugs. In such aspects, the system 100 may be realized as a pin or other small device that may be worn by a user (e.g., on a collar, as part of an earring or other piece of jewelry, and the like). The device may include a chemistry reservoir configured to retain a drug that may be periodically released to administer a dose of the drug to the wearer of the device. In some aspects, rather than, or in addition to administering a drug, the device may release a scent configured to induce a particular reaction by the user. For example, the scent may be designed to have a calming effect on the user. In such aspects, the system 100 may include a heart rate monitor, and dispersion of the calming scent may be trigger upon detecting that the user's heart rate has increased suddenly or exceeds a threshold level.

Figure 6A:
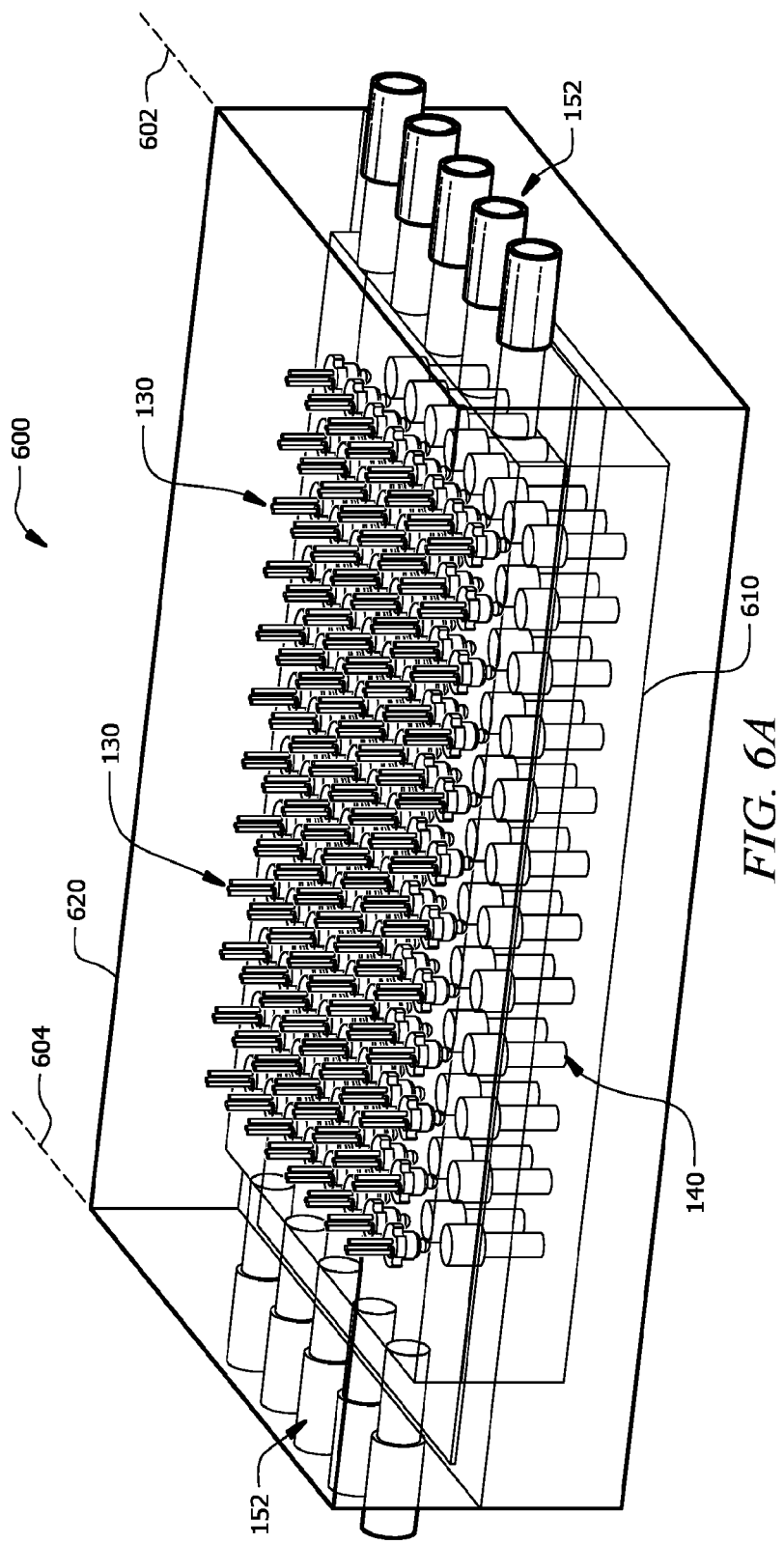
FIGS. 6A and 6B illustrate aspects of an exemplary configuration of chemistry dispersion elements and chemistry reservoirs configured to disperse odorous substances in accordance with an embodiment of the present application.
Figure 6B:
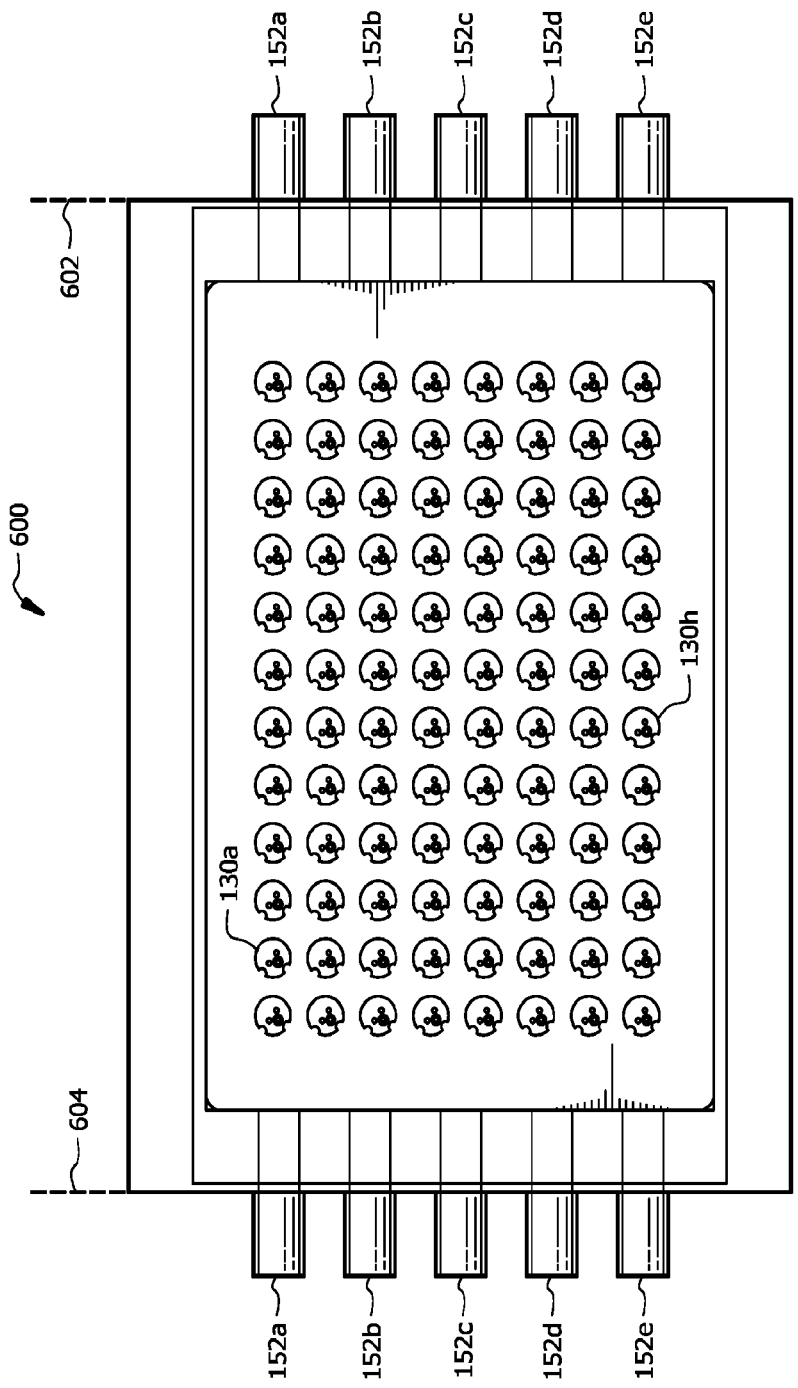

Referring to FIGS. 6A and 6B, aspects of an exemplary configuration of chemistry dispersion elements and chemistry reservoirs configured to disperse odorous substances in accordance with an embodiment of the present application are shown as a configuration 600. As shown in FIG. 6A, in aspects, the plurality of chemistry dispersion elements 130 and the plurality of chemistry reservoirs 140 may be arranged in an array configuration. In the array configuration illustrated in FIG. 6A, the plurality of chemistry reservoirs 140 may be disposed within a cartridge 610. The cartridge may be inserted into a housing 620 in which the plurality of chemistry dispersion elements 130 may be disposed. In this manner, the cartridge may be easily replaced when one or more of the chemistry reservoirs 140 are spent (e.g., the odorous substance retained in at least one of the chemistry reservoirs has been depleted).

In aspects, as illustrated in FIG. 6B, the plurality of chemistry dispersion elements 130 may include one chemistry dispersion element for each of the plurality of chemistry reservoirs. In this manner, activation of one or more of the chemistry dispersion elements 130 may cause the activated chemistry dispersion elements to act upon corresponding ones of the plurality of chemistry reservoirs to disperse the odorous substances retained therein. In aspects, different ones of the chemistry reservoirs may retain different odorous substances for creating different types of smells, which may enable the configuration 600 to generate one or more different smells simultaneously. For example, a first smell may be generated by activating one or more chemistry dispersion elements in row 130a, and a second smell may be generated by activating one or more chemistry dispersion elements in row 130b (e.g., the row immediately below row 130a). The smells generated by the activation of the chemistry dispersion elements 130 in one or more rows may be transported to an air outlet by corresponding airflow pathways 152, as described above with reference to FIG. 3.

In aspects, the plurality of chemistry reservoirs may include multiple chemistry reservoirs that retain the same odorous substances. For example, the plurality of chemistry reservoirs may include a first chemistry reservoir configured to retain a first odorous substance and a second chemistry reservoir configured to retain the first odorous substance. The first chemistry reservoir may include a first well for retaining the first odorous substance and a first permeable membrane covering at least a portion of the first well, and the second chemistry reservoir may include a second well for retaining the first odorous substance a second permeable membrane covering at least a portion of the second well. In aspects, a first quantity of the first odorous substance may be dispersed when a corresponding chemistry dispersion element acts on the first permeable membrane, and a second quantity of the first odorous substance may be dispersed when a corresponding chemistry dispersion element acts on the second permeable membrane, where the first quantity is different from the second quantity such that dispersion of the first odorous substance from the first chemistry reservoir produces a different intensity of the first odorous substance relative to dispersion of the first odorous substance from the second chemistry reservoir.

In an additional or alternative aspect, different intensities of odors may be generated by varying the airflow rate, such as by varying a number of airflow pathways 152a-152e used to transport the dispersed odorous substances to the air outlet. In an additional or alternative aspect, varying the number of airflow pathways 152a-152e may increase the rate at which the odorous substances are delivered to the air outlet for perception by a user, where more airflow pathways 152A-152e are used to provide rapid delivery and a fewer number of airflow pathways 152A-152e are used to provide a slower delivery. In aspects, the airflow pathways 152a-152e may enter the housing 620 on a first side 602 (e.g., a housing airflow inlet) and may exit the housing 620 on a second side 604 (e.g., a housing airflow outlet). It is noted that the particular side in which the airflow enters and exits the housing 620 could be different than is illustrated in FIGS. 6A and 6B. For example, the housing airflow inlet could be on the second side 604 and the housing airflow outlet could be on the first side 602, or alternatively one or more of the housing airflow inlet/outlet could be located at another location relative to the positions illustrated in FIGS. 6A and 6B.

In aspects, the plurality of chemistry dispersion elements may be mounted within the housing 620, such that when the cartridge 610 is replaced, only the plurality of chemistry reservoirs 140 are replaced. If one or more of the plurality of chemistry dispersion elements fail, the housing may be opened to replace the failed chemistry dispersion element(s). In this manner, the configuration 600 provides a cost effective and dynamic arrangement for implementing an aspect of system 100. For example, only replacing the cartridge 610 (e.g., the plurality of chemistry reservoirs 140), rather than both the plurality of chemistry dispersion elements and the plurality of chemistry reservoirs, or only replacing failed chemistry dispersion elements, rather than both the plurality of chemistry dispersion elements and the plurality of chemistry reservoirs, may reduce the costs associated with operating a system (e.g., the system 100) configured to generate one or more smells. Additionally, the configuration 600 provides the capability of replacing the cartridge 610 without having to replace the plurality of chemistry dispersion elements 130, enabling the configuration 600 to be quickly reconfigured with a different cartridge configured with different odorous substances. This may enable the configuration 600 to be quickly and dynamically adapted to different settings. For example, a first cartridge 610 may be configured for a first setting (e.g., a first video game, movie, etc.) and a second cartridge 610 may be configured for a second setting (e.g., a second video game, movie, etc.). Thus, the configuration 600 illustrated in FIGS. 6A and 6B provides dynamic capabilities for a system configured for generating one or more smells. It is noted that the configuration 600 may be communicatively coupled to a controller, such as controller 110 of FIG. 1, that controls the operations of the plurality of chemistry dispersion elements to disperse the one or more odorous substances in accordance with aspects of the present disclosure. Additionally, it is noted that the configuration 600 illustrated in FIGS. 6A and 6B demonstrates that aspects of embodiments enable a plurality of chemistry reservoirs and chemistry dispersion elements to be arranged in a small form factor, which may make the configuration 600 (and system 100) more suitable for certain types of commercial deployments as compared to other systems designed to generate smells. It is noted that the particular number of chemistry dispersion elements, chemistry reservoirs, and airflow pathways illustrated in FIGS. 6A and 6B has been provided for purposes of illustration, rather than by way of limitation, and that in aspects of embodiments, the configuration 600 may be implemented with more or fewer of these components.

Figure 7A:
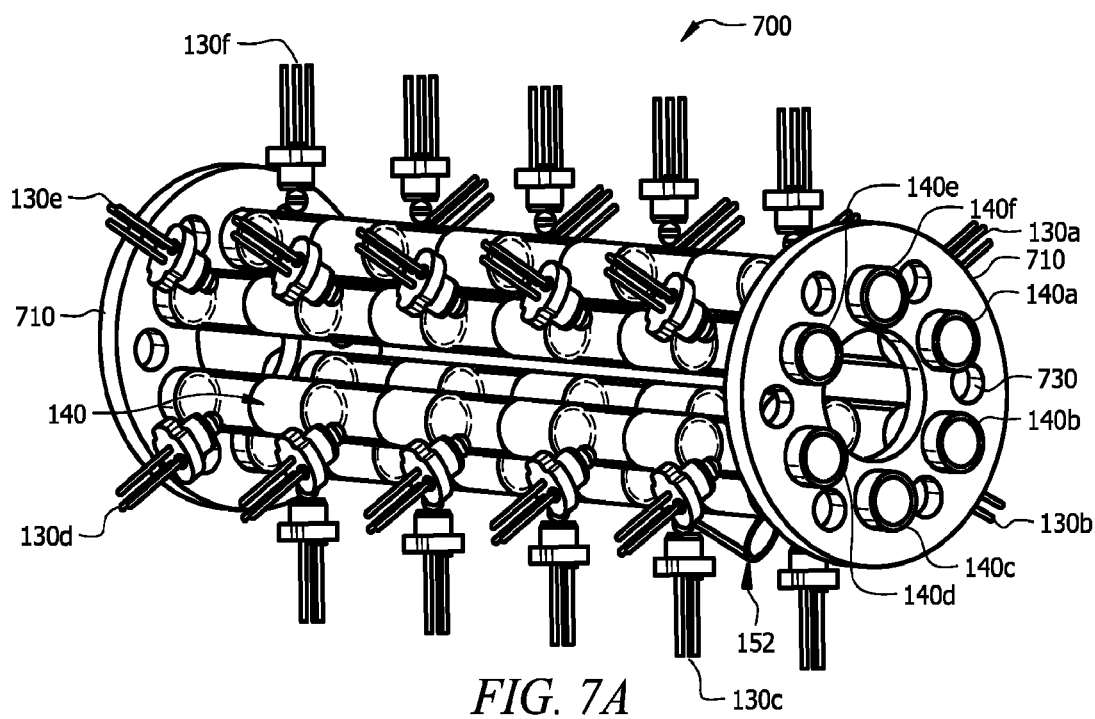
FIGS. 7A and 7B illustrate aspects of an exemplary configuration of chemistry dispersion elements and chemistry reservoirs configured to disperse odorous substances in accordance with an embodiment of the present application.
Figure 7B:
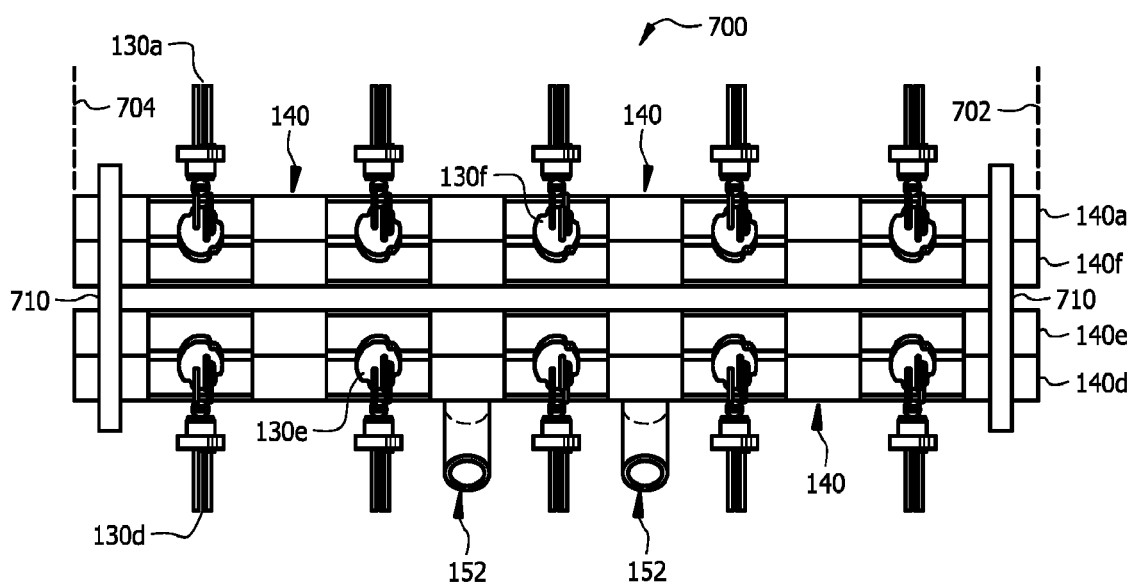

Referring to FIGS. 7A and 7B, aspects of another exemplary configuration of chemistry dispersion elements and chemistry reservoirs configured to disperse odorous substances in accordance with an embodiment of the present application are shown as a configuration 700. As shown in FIGS. 7A and 7B, a plurality of chemistry dispersion elements 130a-130f, and a plurality of chemical reservoirs 140a-140f are provided. In the configuration 700, the plurality of chemical reservoirs 140a-140f are configured as permeable tubes. Sections of each of the permeable tubes may include one or more hollow portions, and each hollow portion may correspond to one chemistry reservoir configured to retain an odorous substance. As described in more detail below with reference to FIGS. 8A and 8B, adjacent hollow sections of each permeable tube may be separated by non-hollow portion (e.g., a capped portion) to prevent mixing of the odorous substances retained within each of chemistry reservoirs. In aspects, the permeable tubes 140a-140f may be formed from polytetrafluoroethylene (PTFE), fluorinated ethylene propylene (FEP), polyether ether ketone (PEEK), ethylene chlorotrifluoroethylene (ECTFE), EFEP, which is a terpolymer (e.g., meaning it is composed of three parts) made from ethylene, tetrafluoroethylene (TFE), and hexafluoropropylene (HFP), ethylene tetrafluoroethylene (ETFE), liquid crystal polymers (LCPs), nylon, polyethylene (PE), polyethylene terephthalate (PET), perfluoroalkoxy (PFA), polyvinylidene fluoride (PVDF), THV, which is a polymer comprised of three different monomers: tetrafluoroethylene, hexafluoropropylene, and vinylidene fluoride, polydimethylsiloxane, nafion, or other materials that enable controlled dispersion of odorous substances retained therein. During operation, the chemistry dispersion elements may act upon an exterior surface of a section of one of the permeable tubes (e.g., a section corresponding to one of the plurality of chemistry reservoirs) to disperse the odorous substance retained in the section of the permeable tube. As illustrated in FIGS. 7A and 7B, the permeable tubes 140a-140f may be arranged in a cylindrical manner and retained in place by retention plates 710. In aspects, the retention plates 710 may be formed from an inert material, such as stainless steel, to prevent contamination of smells generated by dispersion of the odorous substances and/or to prevent damage to the retention plates 710. Additionally, as shown in FIGS. 7A and 7B, airflow pathways 152 may be provided to transport a volume of air configured to mix with odorous substances dispersed from the plurality of chemistry reservoirs associated with the permeable tubes 140a-140f and to transport the dispersed odorous substances to an air outlet, as described in more detail below with reference to FIGS. 10A-10D.

Referring to FIGS. 8A and 8B, aspects of a technique for controlling a chemistry dispersion element to act upon a chemistry reservoir to disperse an odorous substance retained within the chemistry reservoir in accordance with an embodiment of the present application are shown. As shown in FIG. 8A, a permeable tube 140a may include chemistry reservoirs 810 and capped portions 820. The chemistry reservoir 810 may retain an odorous substance that is dispersed when a corresponding chemistry dispersion element 130a acts upon an exterior surface of the permeable tube at a location corresponding to the chemistry reservoir 810. For example, in FIG. 8B, at 802, chemistry dispersion element 130a is in proximity with chemistry reservoir 810, but is not acting upon the surface of the permeable tube and so the odorous substance is retained within the chemistry reservoir. As indicated by arrow 803, a controller (e.g., the controller 110 of FIG. 1) may activate the chemistry dispersion element 130a, as indicated at 804, causing the chemistry dispersion element 130a to emit a signal that acts upon the surface of the permeable tube at the section corresponding to chemistry reservoir 810. As indicated by arrow 805, and as shown at 806, as the chemistry dispersion element 130a acts upon the chemistry reservoir 810, a portion of the odorous substance retained within the chemistry reservoir 810 may be dispersed. As described above, as the odorous substance is dispersed, a volume of air may be used to transport the odorous substance to an air outlet where a smell may be perceived by a user.

Figure 9A:
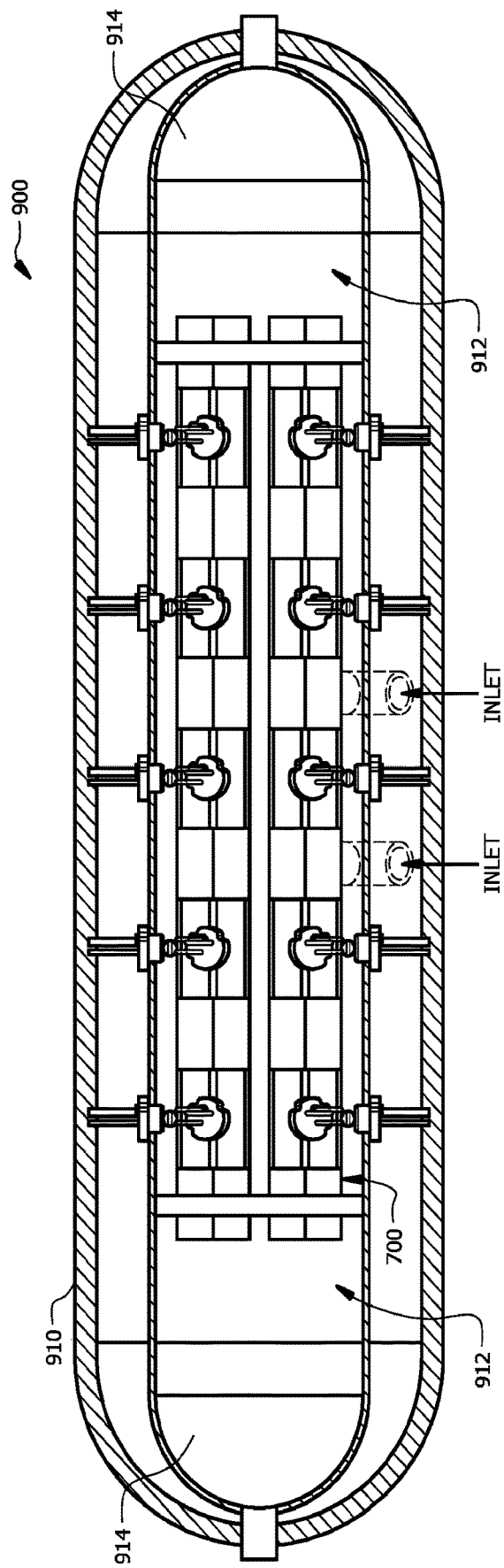
FIGS. 9A and 9B illustrate aspects of an exemplary configuration of chemistry dispersion elements and chemistry reservoirs configured to disperse odorous substances in accordance with an embodiment of the present application.
Figure 9B:
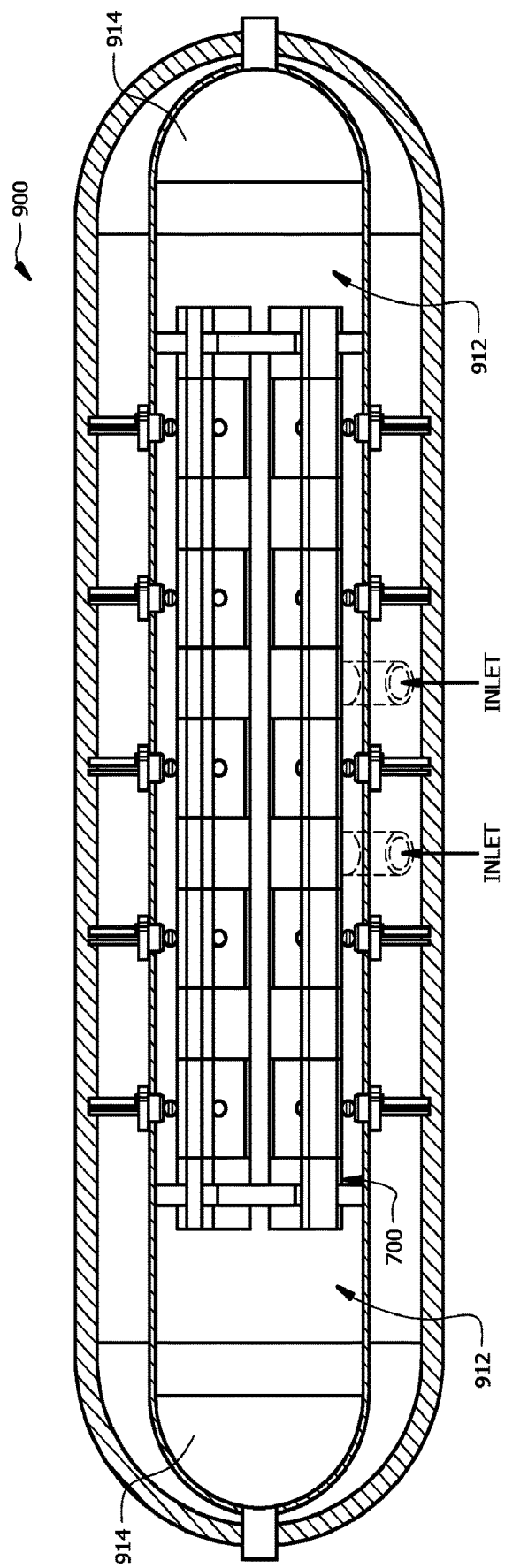

Referring to FIGS. 9A and 9B, aspects of an exemplary configuration of chemistry dispersion elements and chemistry reservoirs configured to disperse odorous substances in accordance with an embodiment of the present application is shown as a configuration 900. As shown in FIGS. 9A and 9B, in the configuration 900 the chemistry dispersion elements and chemistry reservoirs arranged in accordance with the configuration 700 may be disposed within a housing 910. As described above with reference to FIGS. 6A and 6B, in aspects, the housing 910 may retain the plurality of chemistry dispersion elements 130a-130f, and the plurality of chemistry reservoirs (e.g., the permeable tubes 140a-140f) may be inserted into the housing 910. Referring briefly back to FIG. 7A, in aspects, the retention plates 710 may include alignment holes 730. The alignment holes 730 may be configured to align the permeable tubes 140a-140f within the housing 910 such that each chemistry reservoir aligns with one of the plurality of chemistry dispersion elements 130a-130f. It is noted that although FIG. 7A illustrates the mechanism for aligning the permeable tubes 140a-140f within the housing 910 as alignment holes 730, in aspects, other alignment mechanisms may be provided and the alignment holes 730 have been illustrated for purposes of illustration, rather than by way of limitation.

Referring back to FIGS. 9A and 9B, the housing 910 may include a chamber 912 configured to receive the permeable tubes 140a-140f and the plurality of chemistry dispersion elements 130a-130f. Additionally, the housing 910 may include apertures for receiving inlet air from the air pathways 152 and for directing the air to the air outlet. For example, in FIGS. 9A and 9B, the housing 910 includes outlet pathway 914. In aspects, outlet pathway 910 may be configured to generate turbulence as the air passes through toward the air outlet. This may mix the odorous substances with the air to enhance the smell(s) that is perceived by the user. In aspects, the turbulence may be generated by one or more baffles (not shown in FIGS. 9A and 9B) or other mechanisms disposed within the outlet pathway 914. As illustrated in FIGS. 7A-7B and 9A-9B, by providing the plurality of chemistry dispersion elements and the plurality of chemistry reservoirs in accordance with the configuration 700 and the configuration 900, a system for generating one or more smells may be provided in a small form factor while consuming a small amount of power.

Figure 10A:
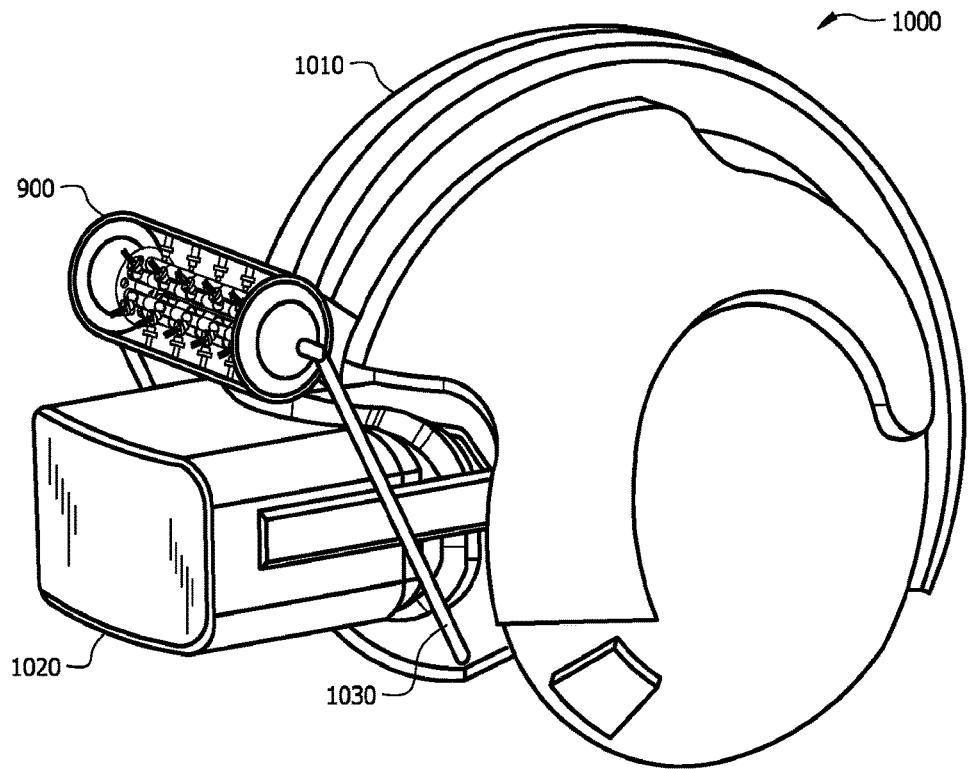
FIGS. 10A-10D illustrate aspects of an exemplary configuration of chemistry dispersion elements and chemistry reservoirs configured to disperse odorous substances in accordance with an embodiment of the present application.
Figure 10B:
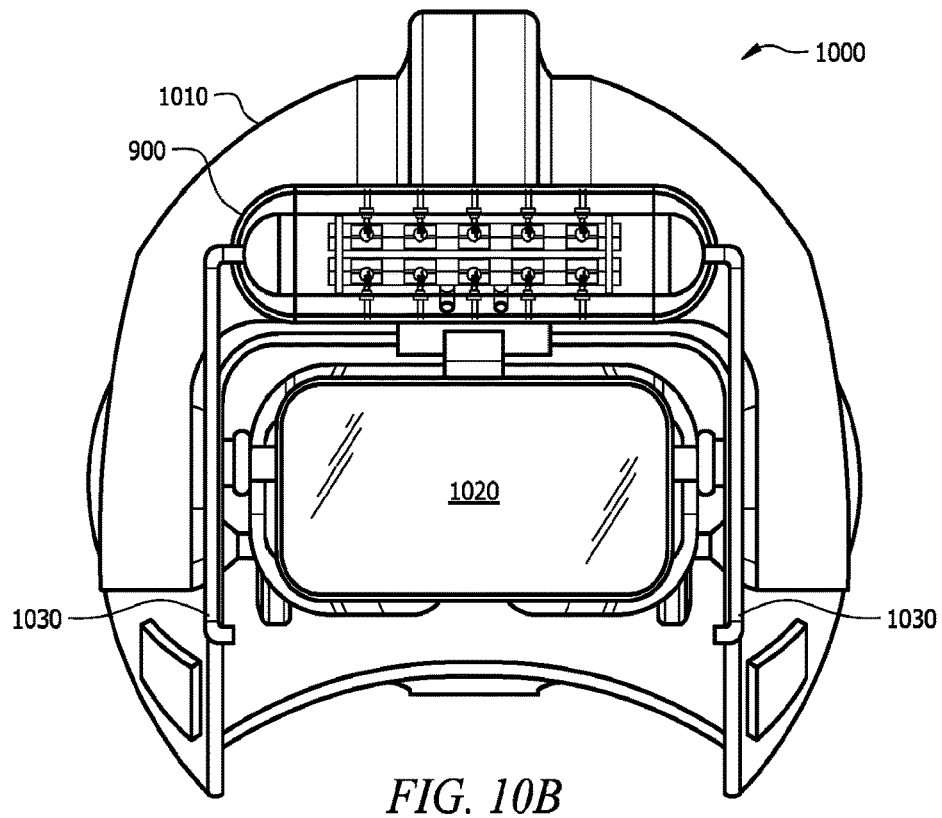
Figure 10C:
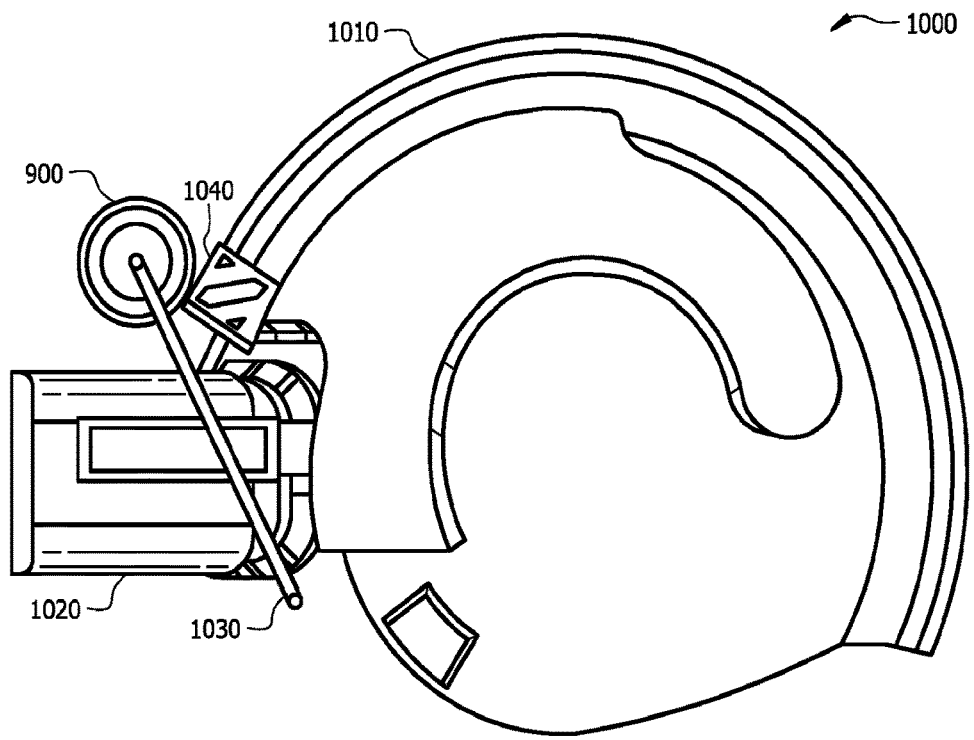
Figure 10D:
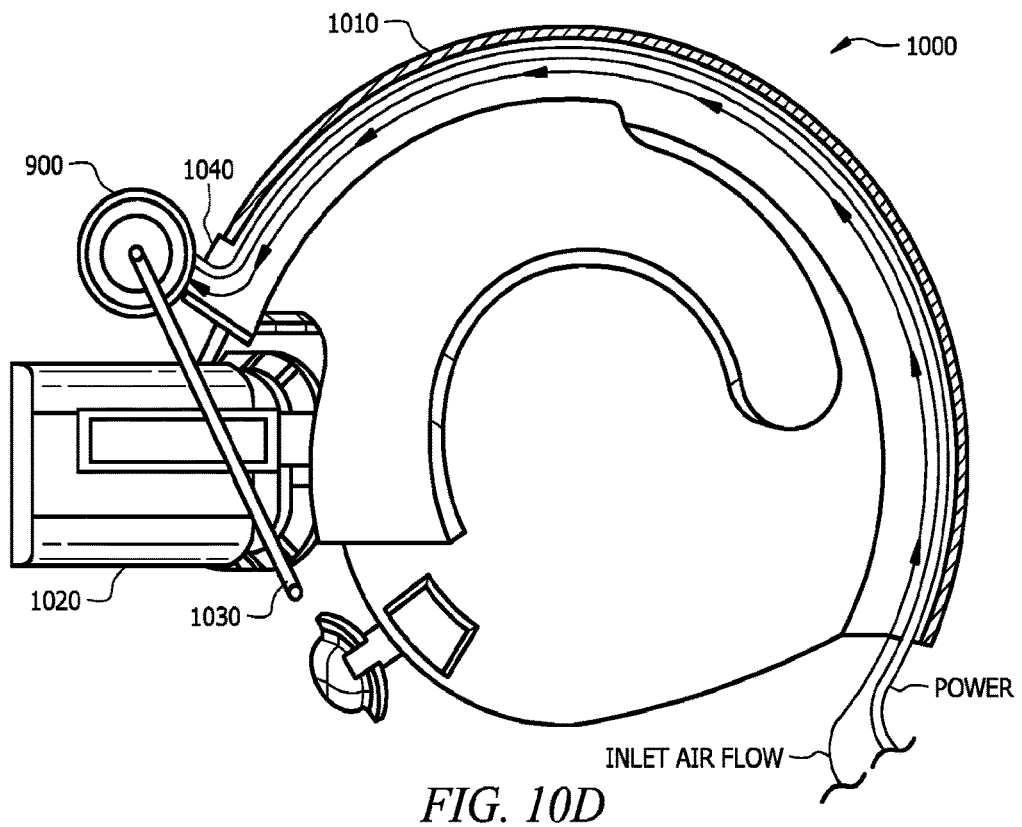

Referring to FIGS. 10A-10D, aspects of an apparatus configured to disperse odorous substances in accordance with an embodiment of the present application is shown as an apparatus 1000. As shown in FIGS. 10A-10D, the apparatus 1000 may include a helmet 1010, a viewing device 1020, and an air outlet positioning device 1030. In the particular embodiment illustrated in FIGS. 10A-10D, the viewing device 1020 is shown as a virtual reality viewing device, however, embodiments of the present disclosure may readily be utilized with other types of viewing devices, such as television screens, movie screens, and the like. Further, although FIGS. 10A-10D illustrate the apparatus 1000 as including the helmet 1010, in other embodiments, the helmet may be omitted. As shown in FIG. 10C, the apparatus 1000 may include a mount 1040 configured to couple the apparatus 1000 to the housing illustrated in the configuration 900 of FIGS. 9A and 9B. In aspects, the air outlet positioning device 1030 may be coupled to the outlet pathway 914. The air outlet positioning device 1030 may be formed to have a hollow core, allowing air to flow from the airflow pathways 152 through the housing 910 to the outlet pathway 914 and then travel through the air outlet positioning device 1030. This may enable the smells generated by dispersing the odorous substances, as described above, to be released proximate the user's nose. In aspects, the air outlet positioning device 1030 may be formed from a flexible material, enabling it to be adjusted to a comfortable position proximate the user's nose. As illustrated in FIG. 10D, the helmet 1010 may include airflow pathways for providing an inlet air flow and may also include power transmission lines for providing power to the plurality of chemistry dispersion elements. In aspects, the power provided by the helmet 1010 may be provided via a battery or another power source (e.g., a plug-based power source) integrated with helmet 101. In aspects, helmet 1010 may also include a controller 100 (not shown) for controlling the dispersion of odorous substances, as described above. As shown in FIGS. 10A-10D, aspects of embodiments provide a configuration that enables a small form factor system for generating smells.

Figure 11B:
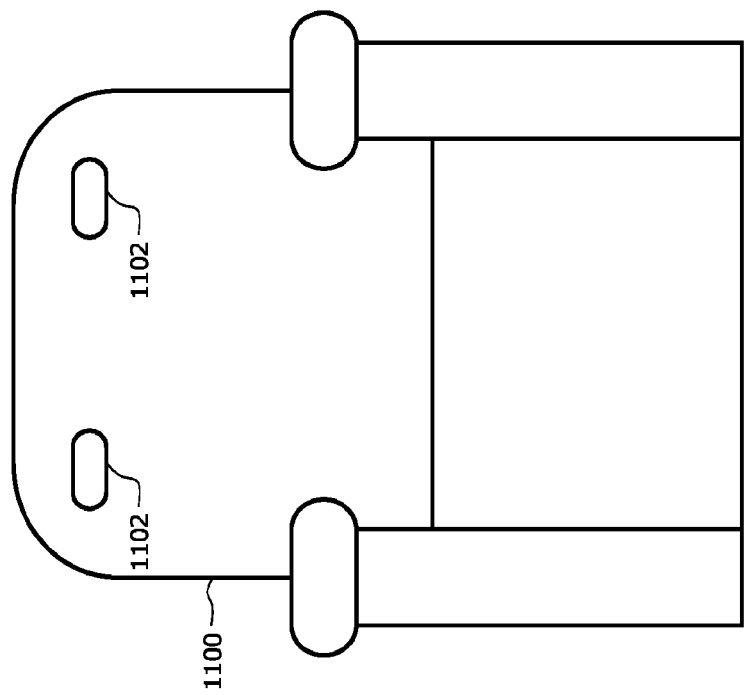
FIGS. 11A and 11B illustrate aspects of an exemplary configuration of chemistry dispersion elements and chemistry reservoirs configured to disperse odorous substances in accordance with an embodiment of the present application.
Figure 11A:
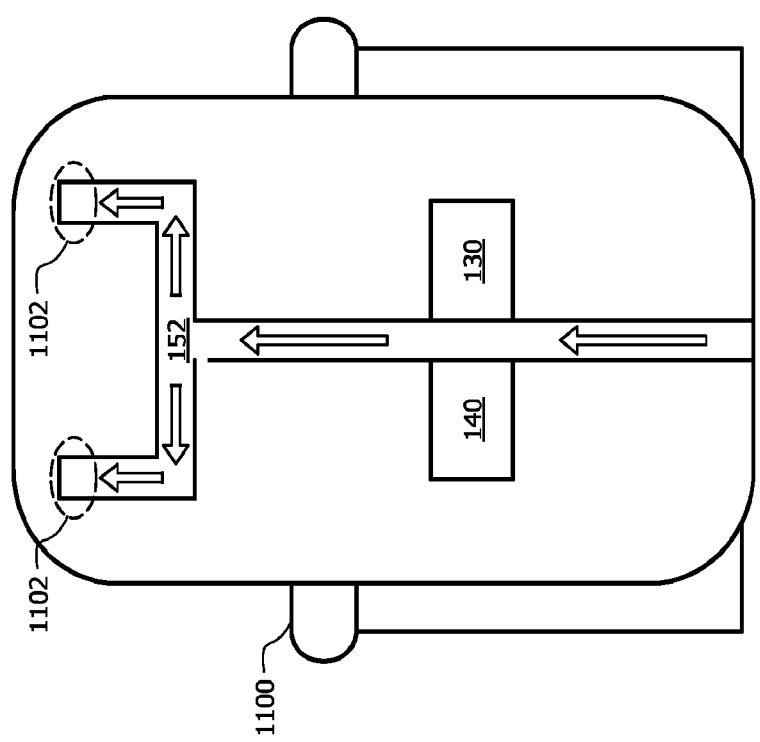

Referring to FIGS. 11A and 11B, aspects of an exemplary configuration of chemistry dispersion elements and chemistry reservoirs configured to disperse odorous substances in accordance with an embodiment of the present application is shown. In FIGS. 11A and 11B, a chair 1100 is shown. In aspects, the chair 1100 may be a theater seat, a gaming chair, or other type of chair from which a user views media content. As shown in FIG. 11A, a back of the chair 1100 may be provided with a plurality of chemistry dispersion elements 130, a plurality of chemistry reservoirs 140, airflow pathways 152, an air pump (not shown), a power source (not shown), and a controller (not shown). The airflow pathways 152 may transport a volume of air past the plurality of chemistry dispersion elements 130 and the plurality of chemistry reservoirs 140, where smells corresponding to one or more odorous substances dispersed by the plurality of chemistry dispersion elements 130 and the plurality of chemistry reservoirs 140 may be picked up and transported to vents 1102 located on the front of the chair 1100, shown in FIG. 11B. In aspects, the plurality of chemistry dispersion elements 130 and the plurality of chemistry reservoirs 140 may be provided in accordance with the configuration 600 of FIGS. 6A and 6B, thereby enabling the chair 1100 to be quickly reconfigured (e.g., by replacing the cartridge 610) to generate different smells depending on the media content to be viewed while a user is sitting in the chair 1100. This may be particularly useful in movie theatres and/or for video game sessions, since media content is often changed frequently.

Figure 12:
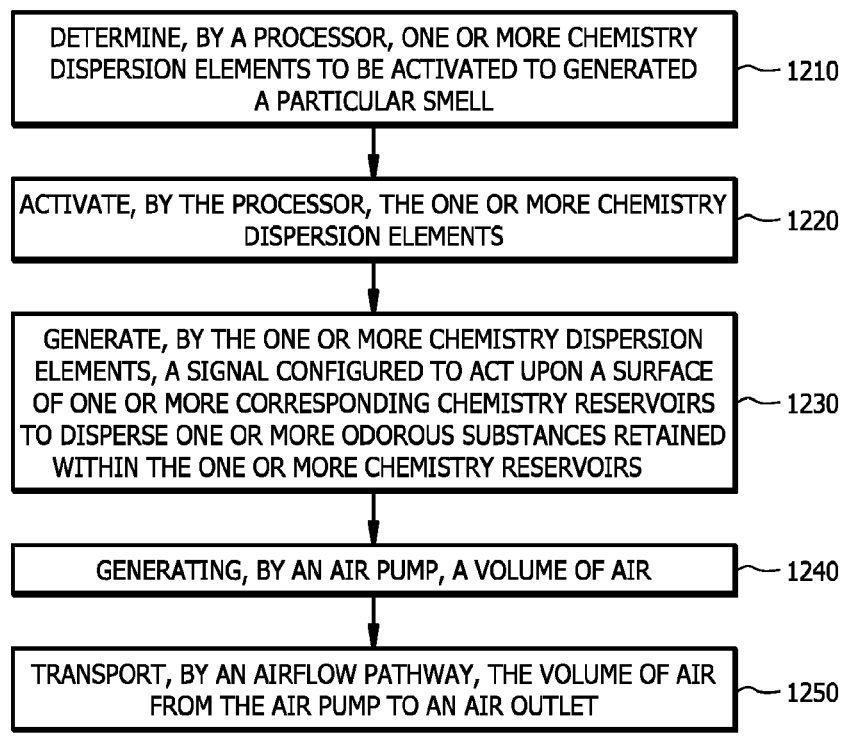
FIG. 12 illustrates a flow diagram of an exemplary method for dispersing odorous substances in accordance with an embodiment of the present application.

Referring to FIG. 12, a flow diagram of a method for selectively generating and dispersing one or more smells in accordance with embodiments is shown as a method 1200. In aspects, the method 1200 may be implemented in software and may be stored on a computer-readable medium as instructions (e.g., the instructions 122 of FIG. 1) that, when executed by one or more processors (e.g., the one or more processors 112 of FIG. 1), cause the one or more processors to perform operations for generating and dispersing one or more smells in accordance with embodiments, as described above with reference to FIGS. 1-10.

At 1210, the method 1200 includes determining, by a processor, one or more chemistry dispersion elements to be activated to generated a particular smell. In aspects, the one or more chemistry dispersion elements that are to be activated may be determined according to information stored in a database, such as the information stored at database 124 of FIG. 1. At 1220, the method 1200 includes activating, by the processor, the one or more chemistry dispersion elements, and, at 1230, generating, by the one or more chemistry dispersion elements, a signal configured to act upon a surface of one or more corresponding chemistry reservoirs to disperse one or more odorous substances retained within the one or more chemistry reservoirs. At 1240, the method 1200 includes generating, by an air pump, a volume of air, and, at 1250 transporting, by an airflow pathway, the volume of air from the air pump to an air outlet. As described above, as the volume of air flows through the airflow pathway(s) from the air pump to the air outlet, at least a portion of the odorous substances dispersed by the one or more chemistry reservoirs may be picked up and transported to the air outlet.

Although embodiments of the present application and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Moreover, the scope of the present application is not intended to be limited to the particular embodiments of the process, machine, manufacture, composition of matter, means, methods and steps described in the specification.

The invention claimed is:

1. A system comprising:
    a plurality of chemistry reservoirs, wherein each of the plurality of chemistry reservoirs comprises a hollow portion of a section of one or more permeable tubes, wherein each of the plurality of chemistry reservoirs is configured to retain an odorous substance within the hollow portion of the section of the one or more permeable tubes, and wherein adjacent hollow portions of the sections of the one or more permeable tubes are separated by non-hollow portions of the section of one or more permeable tubes;
    a plurality of chemistry dispersion elements configured to act upon surfaces of the plurality of chemistry reservoirs to disperse one or more odorous substances from the plurality of chemistry reservoirs;
    a power source configured to power each of the plurality of chemistry dispersion elements;
    a housing, wherein the plurality of chemistry reservoirs and the plurality of chemistry dispersion elements are disposed within the housing;
    an air pump configured to generate a volume of air; and
    an airflow pathway configured to transport the volume of air from the air pump to an air outlet, wherein the volume of air passes through at least a portion of the housing as it flows through the airflow pathway from the air pump to the air outlet, and wherein the volume of air transports at least a portion of the one or more odorous substances dispersed within the housing to the air outlet.

2. The system of claim 1, wherein the plurality of chemistry dispersion elements includes one chemistry dispersion element for each of the plurality of chemistry reservoirs.

3. The system of claim 2, wherein an exterior surface of a section of a permeable tube corresponding to one of the plurality of chemistry reservoirs is the surface upon which a corresponding chemistry dispersion element acts to disperse the odorous substance retained in the section of the permeable tube.

4. The system of claim 3, wherein the each of the plurality of chemistry dispersion elements comprises a laser photodiode configured to act upon the exterior surface of a section of the permeable tube corresponding to one of the plurality of chemistry reservoirs, and wherein the one of the plurality of chemistry reservoirs corresponds to the each of the plurality of chemistry dispersion elements.

5. The system of claim 4, wherein the each of the plurality of chemistry dispersion elements comprises a sapphire ball configured to focus an output of the laser photodiode on the exterior surface of a section of the permeable tube corresponding to one of the plurality of chemistry reservoirs, and wherein the one of the plurality of chemistry reservoirs corresponds to the each of the plurality of chemistry dispersion elements.

6. The system of claim 1, wherein the one or more odorous substances comprise at least one of alkenes, alkanes, alcohols, phenols, aldehydes, esters, acids, aliphatics, aromatics, ketones, and steroids.

7. The system of claim 1, wherein the plurality of chemistry reservoirs comprises:
a first chemistry reservoir configured to retain a first odorous substance, the first chemistry reservoir comprising:
a first hollow portion of a section of the one or more permeable tubes for retaining the first odorous substance; and
a first exterior surface of a section of the permeable tube corresponding to the first chemistry reservoir, wherein the first exterior surface is the surface upon which a corresponding chemistry dispersion element acts to disperse a first quantity of the first odorous substance retained in the first hollow portion; and
a second chemistry reservoir configured to retain the first odorous substance, the second chemistry reservoir comprising:
a second hollow portion of a section of the one or more permeable tubes for retaining the first odorous substance; and
a second exterior surface of a section of the permeable tube corresponding to the second chemistry reservoir, wherein the second exterior surface is the surface upon which a corresponding chemistry dispersion element acts to disperse a second quantity of the first odorous substance retained in the second hollow portion, and wherein the first quantity is different from the second quantity such that dispersion of the first odorous substance from the first chemistry reservoir produces a different intensity of the first odorous substance relative to dispersion of the first odorous substance from the second chemistry reservoir.

8. The system of claim 1, further comprising a controller configured to selectively activate particular chemistry dispersion elements of the plurality of chemistry dispersion elements to generate particular odors.

9. The system of claim 8, further comprising a database storing information that specifies a sequence of smells, wherein the controller selectively activates the particular chemistry dispersion elements of the plurality of chemistry dispersion elements based on the sequence of smells.

10. The system of claim 9, wherein the sequence of smells includes information that identifies an activation sequence for activating, by the controller, particular ones of the plurality of chemistry dispersion elements and timing information that indicates when the controller is to activate each chemistry dispersion element identified in the activation sequence.

11. The system of claim 9, wherein the sequence of odors includes information that identifies a sequence of smells and timing information that indicates when the controller is to generate each smell identified the sequence of smells, wherein the database comprises information that maps smells to particular odorous substances retained within each of the plurality of chemistry reservoirs, and wherein the controller is configured to determine which ones of the particular chemistry dispersion elements are to be activated to generate the sequence of smells in accordance with the timing information.

* * * * *